United States Patent [19]

Brown et al.

[11] 4,393,041

[45] Jul. 12, 1983

[54] FIBRIN BINDER/CARRIER FOR ACTIVE BIOCHEMICAL AGENTS

[75] Inventors: Ross G. Brown; David R. Bright; Robert D. Williams, all of Terre Haute, Ind.

[73] Assignees: International Minerals & Chemical Corp., Terre Haute, Ind.; International Minerals & Chemical Corp., Terre Haute, Ind.

[21] Appl. No.: 143,709

[22] Filed: Apr. 25, 1980

[51] Int. Cl.³ ............................................... A61K 9/24
[52] U.S. Cl. .................................................... 424/19
[58] Field of Search .......................................... 424/19

[56] References Cited

U.S. PATENT DOCUMENTS 4,180,560 12/1979 Katz et al. ............................. 424/19

Primary Examiner—Stanley J. Friedman
Attorney, Agent, or Firm—Steven R. Lammert; H. J. Barnett; Steven R. Lammert

[57] ABSTRACT

An adsorbable fibrin excipient for active biochemical agents which enables controlled release of the biochemical agents when a fibrin pellet or other article containing the biochemical agent is implanted in an animal. Also contemplated are formable combinations of fibrin and other materials, such as lactose, to vary the absorption rate from the rate obtained using fibrin alone.

7 Claims, No Drawings

FIBRIN BINDER/CARRIER FOR ACTIVE BIOCHEMICAL AGENTS

BACKGROUND OF THE INVENTION

This invention relates to absorbable implants for delivering a biochemical agent into the system of an animal in a sustained release over a period of time. Various biochemical agents are conveniently administered to animals by means of subcutaneous implants of pellets which comprise the active biochemical agent and a biocompatible, absorbable excipient. Such biochemical agents which have been administered by means of subcutaneous implants include hormones and anabolic agents for improving growth and feed efficiency in cattle, sheep, pigs and fowl. It is also contemplated that various biochemical agents requiring sustained release can be implanted in horses, dogs, cats, other domestic animals, zoo animals and, in some situations, in wild animal populations. Controlled release of certain hormones can be used to control ovulation in cattle and sheep to schedule breeding programs.

Subcutaneous implanting is advantageous over ad libitum feeding of many biochemical agents because it ensures that a sustained effective dosage of the active biochemical agent is administered to each animal. It is convenient to implant animals such as cattle and sheep on the ear because the pellet is less likely to be dislodged by the animal, and the ear can be discarded when the animal is marketed.

The excipient used in the implant pellet is an important factor in the physiological effect obtained. It should be biocompatible, and nonirritating and dissolve completely without encapsulation to release the active biochemical agent at the desired release rate.

Lactose has long been used as an excipient for implant pellets, and in tablets and pills. Lactose is relatively tasteless, and it is biocompatible. Lactose excipients have been used to administer anabolic agents, such as are described in U.S. Pat. No. 3,196,019 issued July 20, 1965. The active ingredient and the lactose are blended together and pelleted into small spheres or cylindrical shapes containing the desired dosage. Pelleting is conveniently performed on a rotary tableting machine having the appropriate die inserts. The Model B-2 Stokes rotary tableting machine has been used for this purpose to produce pellets having a hardness in the range of 5-10 Strong-Cobb Hardness Units (SCHU).

An implant formulation having a carrier comprising beeswax, zinc stearate, dibutylphthalate (DBP) and polyvinylpyrrolidone (PVP) is described in U.S. Pat. No. 3,428,729. The "DMP" compound is said to be the key to slow the melting of the beeswax and "PVP" and, therefore, to the controlled release of the active ingredient (a hormone to regulate ovulation).

U.S. Pat. No. 3,499,445 is also directed to ovulation control by subcutaneous implant, and describes a 3-layered compressed disc implant pellet which contains chloesterol, carbowax and magnesium stearate as the carrier material for certain steroid compounds. The object again is to obtain a sustained release of the active steroid compound from the composite disc implant. This patent also discloses surgical removal of the implants after 14-18 days to abruptly terminate the treatment.

A polylactide carrier/binder for use in combination with drugs in the form of an implant is described in U.S. Pat. No. 3,773,919 issued Nov. 20, 1973 (See U.S. Pat. No. 3,773,919, column 9, line 59). The term "polylactide" includes a polyester derived from an $\alpha$-hydroxycarboxylic acid and more specifically, the polymer derived from lactic acid ($\alpha$-hydroxypropionic acid). The above carrier material is said to undergo biodegradation in the body into normal metabolic products.

An extensive discussion of various types of implant pellets is found in U.S. Pat. No. 4,180,560 issued Dec. 25, 1979. This patent is directed to a biocompatible, inert core implant having a biosoluble coating comprising a carrier such as polyethylene glycol (PEG) and cholesterol. The inert core materials listed include glass, cellulose acetate, methylmethacrylate, other acrylics, nylon, polypropylene, silicone rubber, PEG and sugar-starch beads.

A fibrin prosthesis useful in surgical procedures is described in U.S. Pat. No. 3,523,807 issued Aug. 11, 1970. The fibrin was obtained from blood plasma by natural clotting through the addition of calcium chloride solution. The clotted plasma was ground and the serum pressed out, and the ground product is washed and dried to provide a fibrin powder. The fibrin powder can be molded into various shapes to be used in surgical procedures such as to strengthen liver-sutures, provide a temporary cap for use in a hip-joint operation and to elevate the urethra in a urogenital surgical procedure.

Bovine fibrin is disclosed as being used for these surgical purposes by Capperauld, et al., Properties of Bovine Fibrin Absorbable Implants, *Surgery, Gynecology and Obstetrics*, Volume 144, pages 3–7 (January 1977). A method of making the fibrin is disclosed which utilizes bovine plasma by first precipitating fibrinogen with ethanol at a low temperature, following a fractional precipitation procedure. The fibrinogen is redissolved and converted into a stabilized fibrin clot by adding calcium chloride. The clot is then minced, washed, purified, pulverized and dried at 150° C. to produce a bovine fibrin powder for the surgical uses described.

SUMMARY

The subject invention utilizes bovine fibrin as biocompatible, absorbable excipient for active biochemical agents which are first mixed together and then formed into spherical or cylindrical pellets suitable for subcutaneous implanting in an animal to be treated. Biochemical agents which may be administered by this method to obtain a sustained release over an extended period of time include anabolic agents such as zeranol and hormones such as estradiol compounds, also used to increase growth and feed efficiency in animals.

DETAILED DESCRIPTION

The following examples illustrate how the invention may be practiced to advantage.

EXAMPLE 1

Tests were made on three castrated male Angus/Hereford calves to observe the absorption characteristics of pellets made with fibrin excipient. The fibrin used for this test was obtained from Novex, Limited, Budapest, Hungary (hereinafter referred to as "NOVEX" fibrin).

The experimental fibrin-containing pellets used in the tests described herein had the following constituents in the amounts listed below:

| Experimental Pellets | |
|---|---|
| Ingredient | Amount (mg) |
| Zeranol | 12 |
| Fibrin | 3.35 |
| Boric acid | 0.55 |
| Magnesium stearate | 0.40 |
| FD & C Yellow | .0065 |
| Total | 16.31 |

The above ingredients were thoroughly blended and then pelleted using a cylindrical die insert in a Model B-2 Stokes Rotary Tableting Machine to form cylindrical pellets containing the above ingredients in the above amounts. The pellets were approximately 0.090 inches in diameter and 0.13 inches in length. The hardness of the pellets was in the range of 5-10 Strong-Cobb Hardness Units, more particularly, about 5.78 SCHU.

Procedure

Three 12 mg dosage experimental pellets using the "NOVEX" fibrin excipient of the subject invention were used to implant the right ears of each of the three castrated male Angus/Hereford calves.

The implant sites were examined by incision sixty-five days after the above implants were made. The pellets containing "NOVEX" fibrin excipient had been completely absorbed. The fibrin excipient was concluded to be completely biocompatible, and gave excellent absorption of the active biochemical agent. It was concluded from the above results that the fibrin excipient is readily absorbable, and can be used as a suitable excipient for subcutaneous implant pellets to administer active biochemical agents to animals.

EXAMPLE 2

The above results were further verified by a second test. Eighteen Angus/Charolais calves were used consisting of fourteen castrated male calves and four female calves. Fifteen of the above calves were implanted in their right ears with three experimental 12 mg pellets (36 mg/calf) containing zeranol and utilizing bovine fibrin as the excipient made as described above. This particular bovine fibrin was obtained from the Nutritional Biochemicals Division of ICN Life Sciences Group, Cleveland, Ohio. The remaining three calves were implanted on their right ears with three experimental 12 mg pellets (36 mg/calf) containing zeranol and utilizing fibrin obtained from Novex Limited,, Budapest, Hungary. This latter material is promoted for use in human surgical procedures. The test calves were examined at 15, 30, 48, 65 and 75 days and the pellets (if palpable) were removed from three calves at each examination date and assayed.

The approximate absorption rate for the experimental pellets containing bovine fibrin were as follows: 73% by weight absorbed at fifteen days, 92% by weight absorbed at thirty days, and 100% by weight had been absorbed by forty-eight days. No difference in absorption rate was observed between the "NOVEX" fibrin and the bovine fibrin (obtained from ICN).

It is contemplated that the absorption rate can be adjusted by using formulas combining mixtures of fibrin and lactose, or other materials such as methylcellulose, collagen, cholesterol, carbowax, beeswax, dibutylphthalate (DBP), polyvinylpyrrolidone (PVP), zinc stearate, polylactides including α-hydroxypropionic acid, polyethylene glycol (PEG), polypropylene (PPG) and sugar-starch combinations.

EXAMPLE 3

The pellets may also be made up in the following formula, and formed into spherical pellets:

| Fibrin-Containing Spherical Pellets | |
|---|---|
| Ingredient | Amount (mg) |
| Zeranol | 12 |
| Fibrin | 2.89 |
| Calcium sulfate | 1.7 |
| Dextrin | 1.28 |
| FD & C Yellow | .01 |
| Boric acid | 0.57 |
| Magnesium stearate | 0.28 |
| Total | 18.73 |

The above ingredients are thoroughly blended, and then formed into pellets on a Stokes Model B2 rotary tableting machine having die inserts to make generally spherical pellets substantially $\frac{1}{8}$-inch (0.125") in diameter and about 0.108 inches in height. The above spherical pellets have substantially the same dosage per pellet as the above described cylindrical pellets, and it could be expected that the dissolution rate would be slightly lower because of the spherical shape of the pellet, but typical pellet hardness is lower (3-6 SCHU), which tends to accelerate the dissolution rate. The two effects cancel each other.

We claim:

1. In a method of administering an active biochemical agent to a living animal over a controlled period of time by subcutaneously implanting in said animal a pellet comprising said active biochemical agent and a biocompatible excipient comprising bovine fibrin, said active biochemical agent being selected from the group consisting of hormones, steroids, estradiol compounds and anabolic agents for promoting growth and feed efficiency in said living animal.

2. In a method of administering an active biochemical agent to a living animal over a controlled period of time by subcutaneously implanting in said animal a pellet comprising said biochemical agent and a biocompatible excipient, the improvement comprising employing a pellet which comprises: 50-80% by weight zeranol; 10-30% by weight bovine fibrin; 0-10% by weight calcium sulfate; 0-10% by weight dextrin; 1-4% by weight boric acid; and 0.5-2% by weight magnesium stearate, said pellet having a Strong-Cobb Hardness Units value in the range of 3-10.

3. The method of claim 1, in which the pellet also comprises an additional biocompatible excipient selected from the group consisting of lactose, collagen, cholesterol, methylcellulose, PEG, PPG, PVP, DBP, beeswax, carbowax, polylactides, magnesium stearate, zinc stearate, starch-sugar mixtures, and combinations of these.

4. In a solid, implantable pellet which includes a biocompatible excipient and an active biochemical agent to be administered to an animal over an extended period of time by subcutaneously implanting the pellet in the animal, said biocompatible excipient comprising bovine fibrin.

5. An implantable pellet comprising: 50-80% by weight zeranol; 10-30% by weight bovine fibrin; 0-10% by weight calcium sulfate; 0-10% by weight dextrin; 1-4% by weight boric acid; and 0.5-2% by weight magnesium stearate, said pellet having a Strong-Cobb Hardness Units value in the range of 3–10.

6. In a biocompatible pelletized controlled release system for an active biochemical agent adapted for subcutaneous implant in a living animal for release of said agent at a controlled release rate into the living animal over a period of time, said release system including a biocompatible excipient comprising 10–90% bovine fibrin in combination with an active biochemical agent compressed into a pellet having a hardness in the range of 3–10 Strong-Cobb Hardness Units, said active biochemical agent being selected from the group consisting of hormones, steroids, extradiol compounds and anabolic agents for promoting growth and feed efficiency in said living animal.

7. The controlled release system of claim 6, including an additional biocompatible excipient to modify the rate of controlled release characteristic of the fibrin, said additional biocompatible material being selected from the group consisting of lactose, collagen, cholesterol, methylcellulose, PEG, PPG, PVP, DBP, beeswax, carbowax, polylactides, magnesium stearate, zinc stearate, starch-sugar mixtures, and combinations of these.

* * * * *